May 30, 1950 H. H. LEWIS Plant Pat. 945
BEGONIA PLANT
Filed May 3, 1949
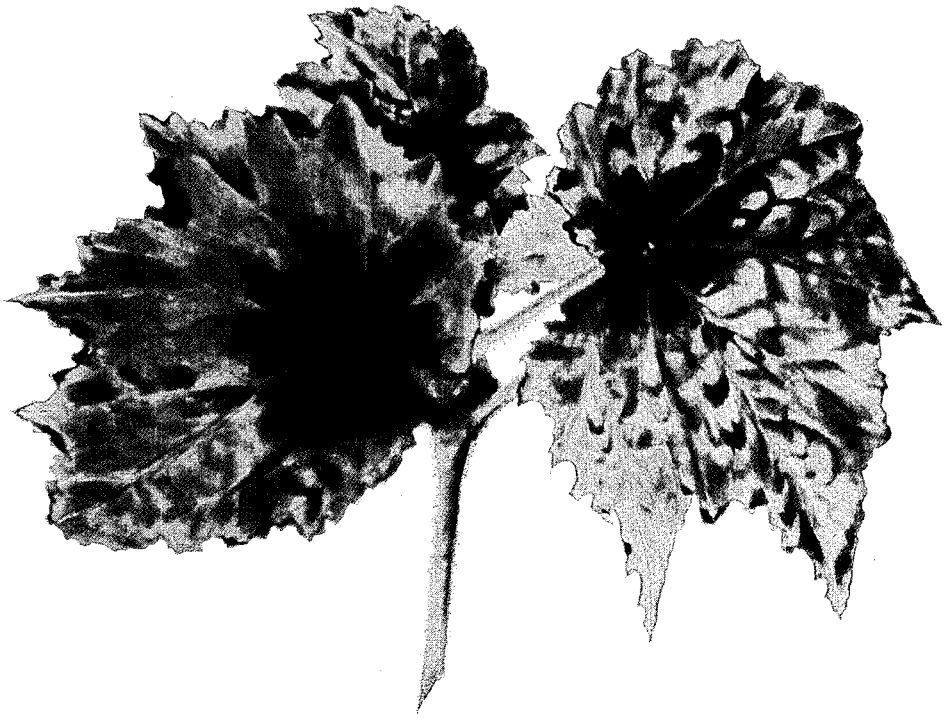
INVENTOR
Helen H. Lewis
By Orville M. Kile
Plant Pat. Agent Patented May 30, 1950

Plant Pat. 945

UNITED STATES PATENT OFFICE

945

BEGONIA PLANT

Helen H. Lewis, Rivera, Calif., assignor to Lewis Gardens, Rivera, Calif.

Application May 3, 1949, Serial No. 91,125

1 Claim. (Cl. 47—60)

The present invention relates to a new and distinct variety of begonia plant of the hybrid type, it being a cross between a rex variety and a fibrous rooted variety. Its male parent was the rex Patsy and the female parent the fibrous Dregii.

Although it has some of the features of each parent, it is very unlike either. Nor is it similar to any other variety known to me.

The most outstanding features of this new variety are the red color and varnished appearance, together with the maple-like shape of the leaf. However, it also has the advantage of low-branching form and attractive pink flowers. It is a rapid grower and is disease resistant.

This new variety has been reproduced asexually by me at our nurseries in Rivera, California, from both leaf and branch cuttings and its characteristics appear to be firmly fixed.

The illustrations show a cluster of the leaves, indicating their shape and color, although their high gloss cannot be shown with the medium used—water colors.

Following is a detailed description of my new variety, color reference being to Ridgway's Color Standards and Nomenclature except where the ordinary dictionary term is obviously intended.

*The plant*

Growth: Vigorous and rapid grower, attaining a height of as much as 24 inches in two years. Easily rooted and propagated both from leaf cuttings and branch cuttings. Although its natural habit of growth is branching, it can successfully be "pinched back" to produce lateral shoots and thus increase the branching and compactness of the plant.

Blooming habit: A spring plant grown from a cutting will bloom the same year. The blooming season is usually in the late summer and fall. After the blooming period, the plant becomes more or less dormant until spring if left to take its natural course. But if forced in a heated greenhouse, it will begin growth again after about a month's dormancy. The flowers appear in loose clusters on different parts of the plant at different times.

Foliage: The showy leaves make a most decorative plant.

*Shape.*—Palmately veined, usually with 7 ribs which are very prominent. Leaf shaped much like a maple leaf except that one of the side lobes is elongated and extended into a point, making the whole leaf rather wing-shaped. Edges are irregularly serrated and slightly ruffled. The narrow lobe and overlapping out at the base make it appear that the stem issues from the back of leaf.

*Size.*—Leaves of a year-old plant measure up to 5½ inches long by 3½ inches at greatest width.

*Appearance.*—Glossy, as if varnished.

*Color.*—Very dark red, between Carmine and Oxblood Red (Plate I), with star (portion surrounding the stem) extremely dark, falling between Burnt Lake (Plate XII) and black. Reverse of leaf is Oxblood Red (Plate I).

*Texture.*—Heavy.

Stems: Sturdy and upright. Same color as leaves. Covered with fine hairs of same color.

*The flower*

Borne: In branching clusters, with both male and female flowers.

Color: Between Begonia Rose (Plate I) and Rose Red (Plate XII).

Shape: Usual for begonias.

Sterility: Sterile so far as is known.

Pedicels or individual flower stems:

*Size.*—Slender but strong. Long. Branching.

*Color.*—Red, between Begonia Rose (Plate I) and Eugenia Red (Plate XIII), but appearing much lighter because of their translucence.

Having thus disclosed my invention, I claim:

The new and distinct variety of hybrid begonia plant, substantially as herein disclosed, characterized particularly by its low-branching habit of growth, the rapidity and ease with which it is propagated and grown, its disease resistance, and the glossy appearance, dark red color and maple-like cut of its medium-sized leaves.

HELEN H. LEWIS.

No references cited.